United States Patent [19]

Soelberg et al.

[11] 4,259,070

[45] Mar. 31, 1981

[54] DENTAL WEDGE SYSTEM

[75] Inventors: Kenneth B. Soelberg, Menlo Park; Marvin M. Stark, Los Altos Hills; Akia Yamaguchi, Los Angeles, all of Calif.

[73] Assignee: Marvin M. Stark Research Foundation, Santa Clara, Calif.

[21] Appl. No.: 97,140

[22] Filed: Nov. 26, 1979

[51] Int. Cl.³ .............................................. A61C 7/00
[52] U.S. Cl. ................................................... 433/149
[58] Field of Search .............................. 433/148, 149

[56] References Cited

U.S. PATENT DOCUMENTS

| 368,988 | 8/1887 | Williams | 433/169 |
| 421,952 | 2/1890 | Marshall | 433/149 |

Primary Examiner—Robert Peshock
Attorney, Agent, or Firm—Lothrop & West

[57] ABSTRACT

A dental wedge system has two interfitting circular-bodied wedges adapted to extend between adjacent teeth and to abut and hold a matrix disposed around one of the teeth.

5 Claims, 7 Drawing Figures

U.S. Patent  Mar. 31, 1981  4,259,070

DENTAL WEDGE SYSTEM

BRIEF SUMMARY OF THE INVENTION

A dental wedge system for retaining a matrix temporarily around a tooth includes a female wedge and a male wedge conveniently of polystyrene. The male wedge has an end disc with a central depression adapted to receive a positioning tool hub projecting from a central tool boss hub. The male wedge also has a stem tapering externally and getting smaller from the end disc toward the stem tip and may also have one or more external, longitudinally extending serrations. The female wedge is generally like the male wedge but has a special stem with a central hollow adapted frictionally to receive and frictionally to engage the male wedge stem.

DETAILED DESCRIPTION

Figure 1:
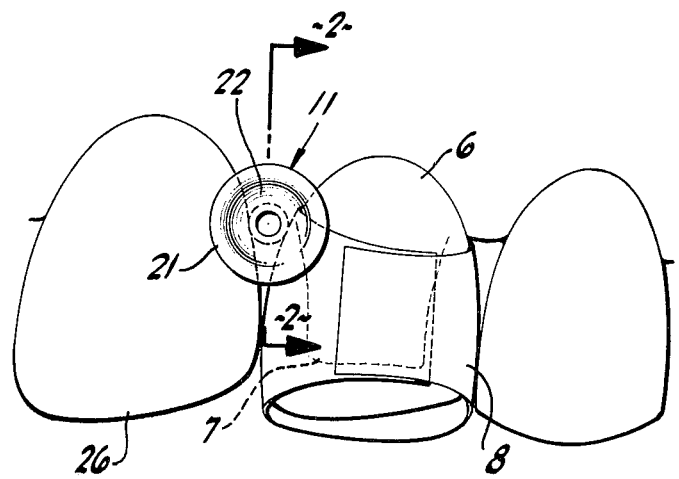
FIG. 1 is a side elevation of a portion of a dental area showing the wedge system in use with a matrix in conducting a restoration, various portions of the view being broken away to reduce its size.
Figure 2:
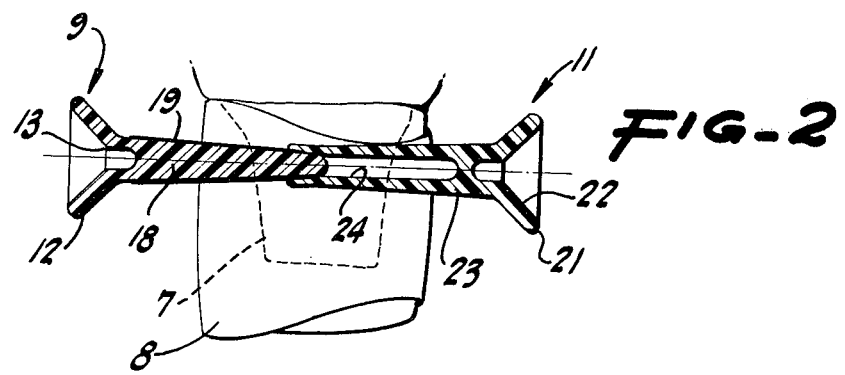
FIG. 2 is a cross-section, the plane of which is indicated by the line 2—2 in FIG. 1.
Figure 5:
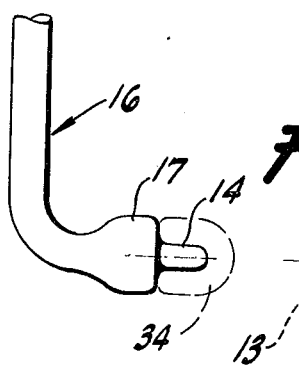
FIG. 5 is a side elevation of a tool, particularly designed for use with the current wedges.
Figures 3, 4:
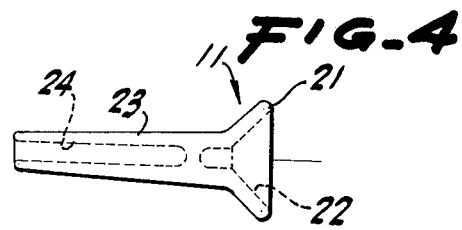
FIG. 3 is a side elevation of a male wedge.
FIG. 4 is a side elevation of a female wedge.

Conducting some dental restorations, particularly those that are in the vicinity of the gum or gingival margin, particularly in the bicuspid and molar region, is often difficult. One of the principal difficulties is that some of the restoration material gets under the gum and can only with considerable trouble be subsequently removed. Such material should be removed, for otherwise that foreign material distorts the gum or gum margin and tends to admit extraneous, highly deleterious substances.

In positioning restoration materials, it is customary to provide a matrix around the prepared tooth being worked on, the aim being to situate the margin of the matrix very close to the surface of the tooth and distinct from the gum in order that the restoration material cannot extrude into undesirable areas. This, however, has been quite difficult to accomplish under many conditions.

In accordance with the present invention, I provide a wedge system, including both male and female wedges. These are effective to hold the matrix in place on the tooth with little or no place for escape of the restoration material between the matrix and the tooth itself.

As shown particularly in the drawings, a tooth 6 is being restored. After having been given its pre-restoration shape 7, it is surrounded by a matrix 8. This primarily is a band of very thin, flexible steel. This is wrapped around the remaining tooth shape 7 and is somewhat overlapped in order to make a very close fit around the base of the tooth.

Particularly to hold the so-set matrix in position throughout the restoration work, I provide a pair of wedges 9 and 11. The wedge 9 is preferably made up of polystyrene or comparable, slightly yielding material and has a tool-engaging disc 12 at one end. This disc has a central depression 13 designed to interengage and fit with a comparable projection 14 on a tool 16. This is especially designed for temporarily receiving and carrying and releasing wedges; for example, the male wedge 9. The tool itself has a boss 17 of about the same diameter as the disc 12 of the wedge. The fit between the projection 14 and the depression 13 is such that while the wedge can quite readily be carried and transported and positioned, there is still an easy release between the positioned wedge and the special tool 16.

Extending from the disc 12, the male wedge has a stem 18 that tapers around and along the general axis of the wedge, being somewhat smaller at the free end than near the disc end. The tapered portion also has one or preferably several outstanding serrations 19 extending longitudinally and being slightly deformable.

To cooperate with the male wedge, the similar female wedge 11 has a comparable disc 21 with a comparable depression 22. This also is able closely to fit the tool 16. Furthermore, the wedge 11 has an extended, externally tapering stem 23 getting smaller toward the point. Also, the stem 23 is provided with an internal recess 24 of approximately a cylindrical configuration and designed to receive and interfit with the stem 18 with a relatively tight frictional engagement.

In the use of the wedges, the tooth is first surrounded with the steel band 8, which is overlapped somewhat and is positioned quite tightly against the remaining tooth structure. When the matrix has been so positioned and the band tightened, the band is held tightly by first positioning the female wedge 11 in position between the matrix and the adjacent tooth 26. To cooperate with the female wedge and to make sure that the female wedge stays well in position without shifting and also to assist in holding the band 8 in position, the male wedge is then introduced into the opening 24 of the female wedge and the two wedges are caused to telescope tightly and with very good frictional interengagement therebetween. The tendency of the male wedge is to expand slightly the otherwise free end of the female wedge so that the steel band is afforded an area of tight tooth contact of considerable extent and so that the steel band or matrix cannot slip with respect to the tooth portion with which it is in engagement.

Figure 7:
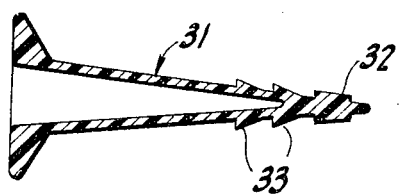
FIG. 7 is a cross-section through a modified form of male wedge.
Figure 6:
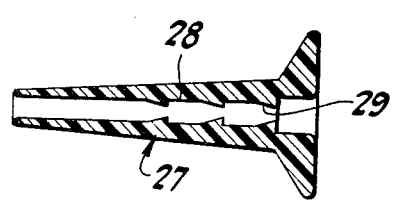
FIG. 6 is a cross-section through a modified form of female wedge.

In some instances, the wedges are modified for firmer interlocking. Instead of depending entirely on a relatively flat cone angle, the wedges are provided with special interengaging means. As specially shown in FIGS. 6 and 7, a female wedge 27 in some parts of its interior surface 28 is provided with several inwardly extending lugs 29. These, like the material of the rest of the wedge 27, are slightly flexible or deformable. Also, a male wedge 31 not only has a solid, shouldered tip 32, but also at suitable intervals on its exterior surface has a number of externally extending lugs 33. With this arrangement, the two wedges are assembled as previously described with the further attribute that appropriate ones of the lugs 29 and 33 interengage or interlock firmly to hold the wedges against separating at random. Even so, when the wedges are to be separated at the end of the operation, either one can be engaged by a tool 16 and in that way can be pulled from the other wedge, the lugs being readily yieldable or disengageable under the manipulation of the tool 16. The tool 16 itself is sometimes provided with a detachable relatively soft tip 34, which may be used with any of the forms of wedges.

The necessary dental work then continues. When such work has been completed, the tool 16 is utilized again to withdraw the male wedge from its position of engagement with the female wedge, which in turn is so removed from the matrix. Thereupon the matrix itself is stripped from the tooth, and the dentist proceeds to clean up the restoration.

It has been found in extensive practice that the wedges as described are quite effective to aid in positioning and holding the matrix, particularly in keeping the edge of the matrix near the gum line quite tightly against the tooth structure so that restoration materials do not escape between the two. This makes the clean-up or final dressing operation relatively simple and provides an excellent job.

We claim:

1. A dental wedge system comprising a female wedge including a tool-engaging disc having a central depression and a female stem having a central hollow, said stem tapering externally from a relatively large merger with said disc to a relatively small free end, and a male wedge including a tool-engaging disc having a central depression and a male stem tapering externally from a relatively large merger with said disc to a relatively small free end, said male stem being receivable in said central hollow of said female stem and frictionally engageable therewith.

2. A device as in claim 1 in which at least one of said wedges is provided with superficial irregularities adapted to interengage with another of said wedges.

3. A device as in claim 1 in which said male stem has at least one outwardly extending and deformable serration.

4. A device as in claim 1 in which at least one of said wedges is of polystyrene.

5. A device as in claim 1 in which said tool-engaging disc having a central depression is adapted temporarily to engage and to be supported on a tool having an end hub with a central tapered boss projecting therefrom.

* * * * *